(12) United States Patent
Yu et al.

(10) Patent No.: US 6,264,665 B1
(45) Date of Patent: Jul. 24, 2001

(54) SYSTEM FOR OCULAR ULTRAMICROSURGERY

(75) Inventors: Dao-Yi Yu; Ian Jeffrey Constable; Stephen John Cringle, all of Nedlands (AU)

(73) Assignee: The Lions Eye Institute of Western Australia Incorporated, Nedlands (AU)

( * ) Notice: Subject to any disclaimer, the term of this patent is extended or adjusted under 35 U.S.C. 154(b) by 0 days.

(21) Appl. No.: 09/171,349

(22) PCT Filed: Apr. 17, 1997

(86) PCT No.: PCT/AU97/00238

§ 371 Date: Oct. 16, 1998

§ 102(e) Date: Oct. 16, 1998

(87) PCT Pub. No.: WO97/38652

PCT Pub. Date: Oct. 23, 1997

(30) Foreign Application Priority Data

Apr. 17, 1996  (AU) .................................................. PN9290

(51) Int. Cl.[7] .................................................. A61B 19/00
(52) U.S. Cl. .......................................... 606/130; 600/104
(58) Field of Search .................................. 606/4, 5, 130, 606/167; 600/104, 111, 558; 128/903

(56) References Cited

U.S. PATENT DOCUMENTS

| 4,562,463 | * | 12/1985 | Lipton ..................................... 358/88 |
| 4,583,117 | * | 4/1986 | Lipton et al. ........................... 358/92 |
| 4,744,362 |   | 5/1988 | Grundler . |
| 4,848,340 | * | 7/1989 | Bille et al. ............................ 128/903 |
| 5,098,426 | * | 3/1992 | Sklar et al. ............................. 606/5 |
| 5,162,641 | * | 11/1992 | Fountain ............................ 250/201.2 |
| 5,368,015 | * | 11/1994 | Wilk ..................................... 128/903 |
| 5,399,951 |   | 3/1995 | Lavallee et al. . |
| 5,410,638 |   | 4/1995 | Colgate et al. . |

FOREIGN PATENT DOCUMENTS

| 4310842 | | 10/1994 | (DE) . | |
| WO 93/09738 | * | 5/1993 | (WO) | ................................... 606/130 |
| 93/13916 | | 7/1993 | (WO) . | |
| 94/26167 | | 11/1994 | (WO) . | |
| WO 95/27453 | * | 10/1995 | (WO) | ................................... 606/130 |
| 97/00649 | | 1/1997 | (WO) . | |

* cited by examiner

Primary Examiner—Pedro Philogene
(74) Attorney, Agent, or Firm—Larson & Taylor PLC

(57) ABSTRACT

A system (10) for ocular ultramicrosurgery a ring (12) for immobilising eye (14) of a patient. The incision point (P) on the eye (14) for surgical tools is marked by a marker (16) that is generated by intersecting tire beams of lasers (104 and 106). The intersection point of the laser beams is fixed in space. In order to move the patient's eye (14) so that point (P) coincides with that fixed point in space, the patient's head (52) is fixed to a head positioner (24). The head positioner is operated by a surgeon (26) through joystick (34) and computer (32) to ensure registration of point (P) and the point designated by the intersecting laser beams. All surgical tools used in the system (10) are supported, positioned and operated or worked by a tool support and positioning system (18). The system (18) comprises a stereotactic manipulator (20) and a tool translation table (22) which is supported on the manipulator (20). The manipulator (20) is used to position a surgical tool (50) on table (22) so that tip (51) of the tool (50) can be aligned with point (P). Thereafter, the manipulator (20) and/or table (22) can separately or in combination be used to pivot the tool (50) about point (A) so that the tip (51) of the tool is positioned at any desired location within the eye and subsequently worked or operated to perform ultramicrosurgery. Surgeon (26) is able to control the manipulator (20) and table (22) via computer (32) and input devices such as joysticks (34, 35) and keyboard (36). In this way, the surgeon's hands are isolated from the movement of the tool (50).

10 Claims, 8 Drawing Sheets

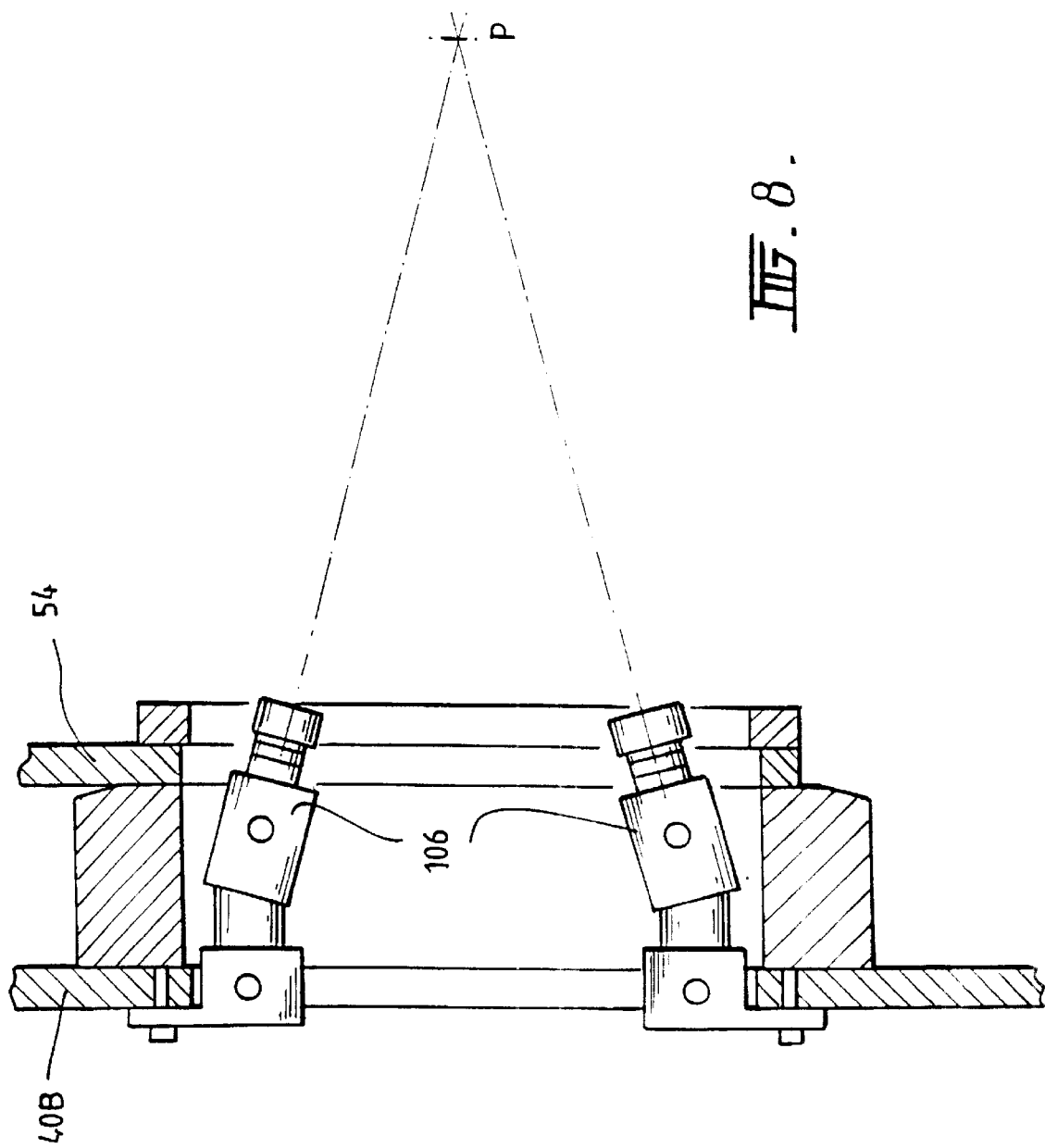

SYSTEM FOR OCULAR ULTRAMICROSURGERY

FIELD OF THE INVENTION

This invention relates to ultra fine surgery, in particular to surgery apparatus to assist an ocular surgeon in delicate ocular ultramicrosurgical operations, typically on or near retinal tissue, the optic nerve and the anterior chamber.

BACKGROUND OF THE INVENTION

The retina is a very small tissue lining the back inside surface of the eye. It is only 0.25 to 0.3 mm thick but 15 sq cm in area. In western countries, disease of the retina is the main cause of untreatable blindness. There is a vital need to be able to deliver biological treatments or operations to precisely determined retina locations and at specific depths, such as into blood vessels or to particular cells of the retina with a precision better than 5 microns. Currently there is no way such biological treatments or operations can be achieved with such accuracy, thus hindering specific drug and other treatments of the retina. The alternative of delivering drugs through the systemic circulation is not possible when only a small region of the retina is targeted, and delivery of powerful drugs into the ocular contents rather than at a particular location in the retina can have unwanted effects.

Current ocular ultramicrosurgical operations, where it is sought to perform delicate manipulations on areas of tissue as small as a few microns in diameter, have had a limited success rate due to the inability of surgeons to accurately control surgical tools using manual manipulations under the microscope. Even the steadiest hand has an unavoidable physiological tremor which at rest has an amplitude of about 50 micrometers and a frequency of between 7 and 12 cycles per second. After 30 minutes of activity, this physiological tremor increases to an amplitude of 2 to 5 mm at a frequency between 4 and 6 cycles per second.

In ocular research laboratories, retinal arterial or venous occlusion has been treated (mainly in animals) by in vivo cannulation of the vessel and injection of clot-clearing agents such as tissue plasminogen activator (tPA), [ Allf and de Juan Jr 1987]), but application of the technique in routine surgery on humans has been prevented by the very low success rate of such operations, typically 20 percent or lower. The low success rate is due in the case of arterial or vein occlusions to the damage done by the surgeon to the blood vessel when micro cannulation is attempted, the micro cannulation device being relatively substantial (typically 20 to 50 microns) compared with the size of the blood vessel (typically about 100 microns).

Hunter et al [ Hunter et al 1994] have described a sophisticated teleoperated microsurgical robot adapted to automation of corneal and lens operations. This system is not adapted to automation of ultramicrosurgical retinal operation.

Manual systems which assist the eye surgeon, particularly in animal experimentation, have been known for a number of years and incorporate stereotactic systems to support surgical tools such as micropipettes in a manner such that the tool shaft is orientated about a pivot point coincident with the point of entry of the tool into the ocular cavity at the pars plana. [ Toth et al 1992, Benner et al 1993]. Such systems do not completely isolate the physiological tremor from the tip of the surgical tool, and since they are manual in nature result in time consuming operations, reducing the practicality of routine application to human surgery.

SUMMARY OF THE INVENTION

It is an object of the present invention to provide a system for ocular ultramicrosurgery which isolates the hands of a surgeon from the patient and provides increased positioning accuracy and speed to make practical the routine application of ultramicrosurgical operations to the eye.

According to the present invention there is provided a system for ocular ultramicrosurgery comprising:

means for immobilising an eye of a patient on which ultramicrosurgery is to be performed;

means for marking the position of a predetermined point on said eye;

tool support and positioning means for supporting a tool in a manner so that said tool can be moved with positional accuracy; and, remote control means for remotely controlling the position and operation of said tool, said remote control means physically isolating the hands of a surgeon from said tool;

whereby, in use, a surgeon can, by means of said remote control means, position a tip of said tool to enter said eye at said predetermined point and to pivot said tool about said predetermined point so that the tip of the tool can be positioned at any desired location within the eye and subsequently operated to perform ultramicrosurgery.

Preferably said means marking the position of a predetermined point comprises means for defining a point in space.

Preferably said system further comprises means for moving said eye and said point in space relative to each other so that said point in space can be bought to coincide with said predetermined point.

Preferably said means for defining said point in space comprises at least two lasers supported in different planes and arranged so that their respective laser beams intersect in space, said point in space being the point of intersection of said laser beams.

Preferably said means for moving said eye and said point in space relative to each other comprises head fixing means for fixing the position of a head of the patient and, means for moving said head fixing means in three orthogonal planes under control of said remote control means.

Preferably said tool support and positioning means comprises: a stereotactic manipulator providing two degrees of freedom of movement of said tool; and, a tool translation table supported on said stereotactic manipulator providing at least one further degree of freedom of movement of said tool and to enable said tool to be moved linearly into and out of said eye through said predetermined point.

Preferably said tool translation table is supported with at least one degree of freedom on said stereotactic manipulator so that the position of a tip of said tool can be adjusted to compensate for defects in the structure or form of the tip.

Preferably said tool translation table is further provided with at least one actuator under control of said remote control means to operate or otherwise work said tool.

Preferably one pair of lasers is supported on said tool translation table, said one pair of lasers arranged so that their respective laser beams mutually intersect each other at said predetermined point; and, a second pair of lasers is supported on said stereotactic manipulator in a plane different to that containing said one pair, said second pair of lasers arranged so that their respective laser beams mutually intersect each other at said predetermined point.

Preferably said remote control means comprises a computer operatively associated with said tool support and position means, said computer provided with a joystick and/or keyboard for receiving instructions from a surgeon to manipulate and control the position and operation of said tool.

BRIEF DESCRIPTION OF THE DRAWINGS

Embodiments of the present invention will now be described by way of example only with reference to the accompanying drawings in which.

DETAILED DESCRIPTION OF PREFERRED EMBODIMENTS

Figure 1:
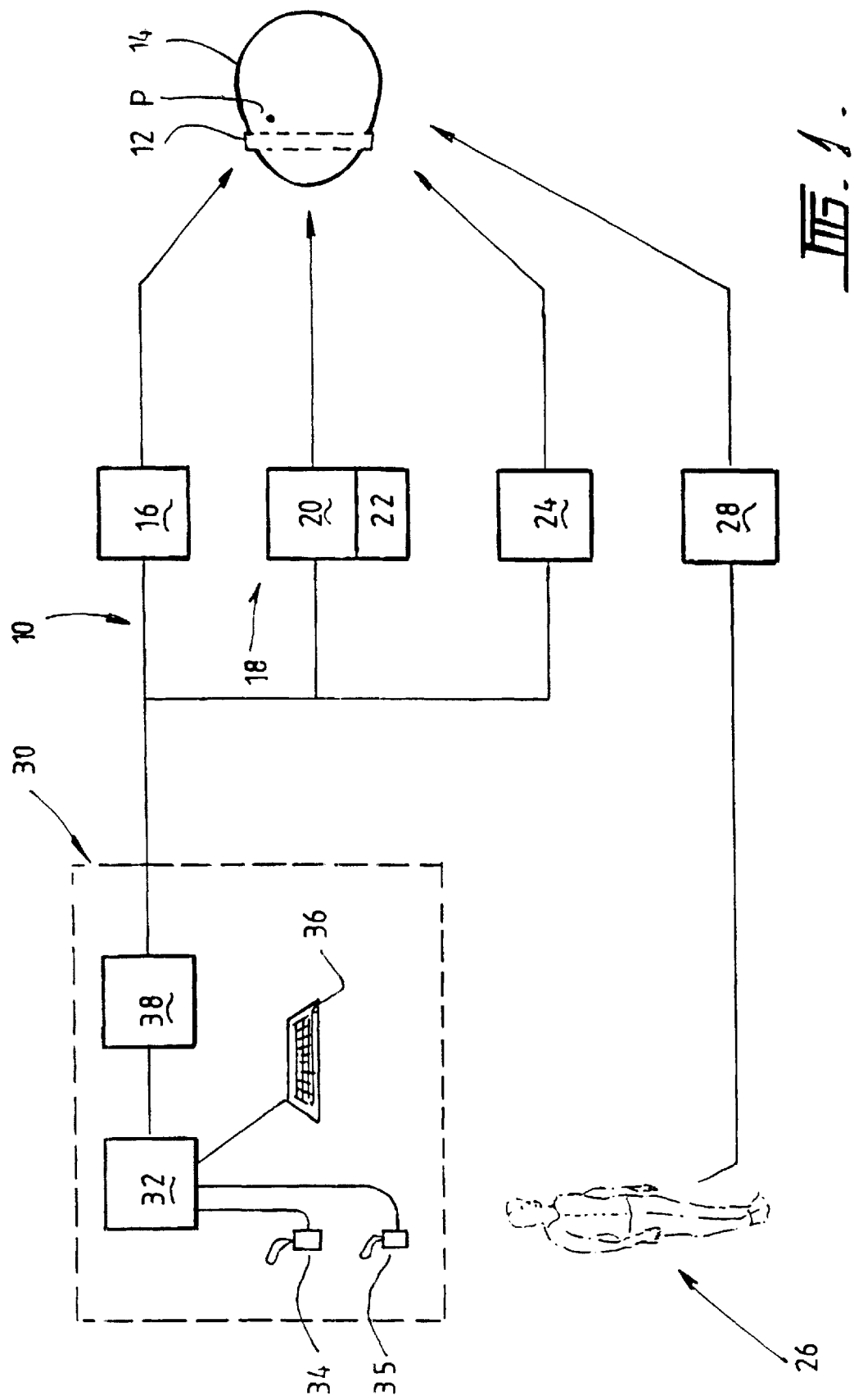
FIG. 1 is a functional block diagram of an embodiment of a system for ocular ultramicrosurgery in accordance with the present invention.

FIG. 1 illustrates a functional block diagram of an embodiment of a system 10 for ocular ultramicrosurgery. The system 10 includes a means 12 for immobilising an eye 14 of a patient on which ultramicrosurgery is to be performed. The means 12 for immobilising the eye is typically in the form of an eye ring which will be clamped to a patient's eye 14 prior to surgery commencing.

It is known that when performing eye surgery, it is preferable for surgical tools to be inserted through one of the four positions on the sclera known as the pars plana for retina and optical nerve, or cornea for the anterior chamber. Marker 16 is used to mark one of the four available positions P at which an incision can be made and surgical tools passed through the sclera of the eye 14 into the ocular cavity.

All surgical tools used in the ultramicrosurgery system 10 are supported, positioned and operated by tool support and positioning means 18. The tool support and positioning means 18 in turn comprises a stereotactic manipulator 20 and a tool translation table 22 supported on the manipulator 20. The stereotactic manipulator 20 can be used to position a surgical tool on the tool table 22 so that the tip of the tool can be aligned with point P on the eye 14. The tool translation table 22 is then operated to move a tool linearly into the eye 14 through point P. Thereafter, the stereotactic manipulator 20 and/or the tool table 22 either separately or in combination can be used to pivot the tool about point P so that the tip of the tool is positioned at any desired location and subsequently operated to perform ultramicrosurgery.

Normally, when a patient is fixed to the system 101 point P does not coincide with a point in space marked by the marker 16. In order that the marker 16 visually mark point P on the eye 14, the head of a patient is moved by a head positioning means 24 so that the marker 16 accurately marks point P on the eye 14. Surgeon 26 is able to visualise the exterior and interior of the eye 14 through an operation microscope 28 focussed on the eye 14. Visualising the eye 14, surgeon 26 can manipulate a tool held on the tool support and positioning means 18 by remote control means 30. The remote control means 30 includes a computer 32 and control input devices, joysticks 34 and 35 and keyboard 36. Measurement and control unit 38 which is part of the remote control means 30, interfaces between the computer 32 and the marker 16, stereotactic manipulator 20, tool translation table 22, and head positioning means 24. The measurement and control unit 38 controls each of these items via instruction from the computer 32 and also provides the computer 32 with operational status of these devices.

Figure 2:
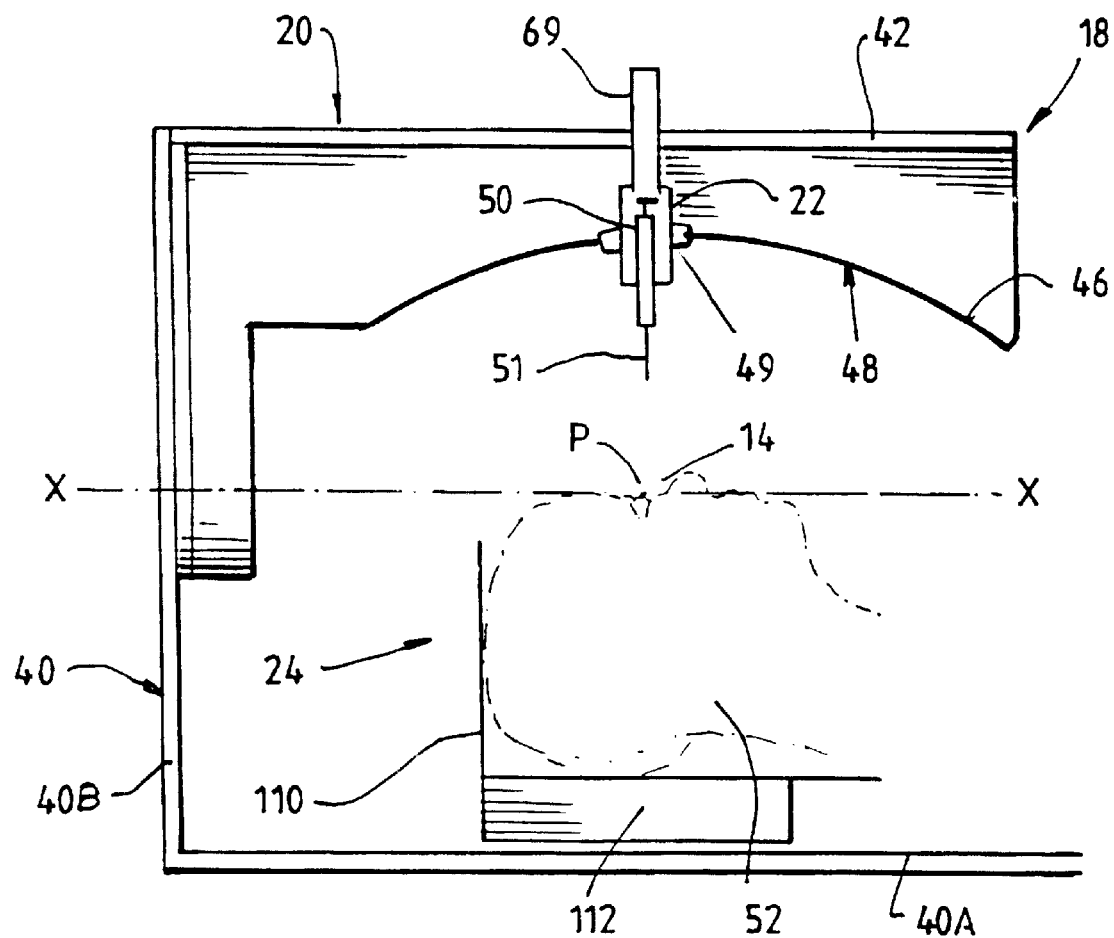
FIG. 2 is a schematic representation of a tool support and positioning means and a head fixing means of the system shown in FIG. 1.

FIG. 2 illustrates in schematic and very simplified form the structure of, and typical positional relationship between, eye ring 12, stereotactic manipulator 20, tool translation table 22, head positioning means 24, and point P of eye 14.

Stereotactic manipulator 20 comprises an L-shaped base 40 comprising a bottom plate 40A which lies in a horizontal plane and an upright plate 40B which extends in a vertical plane. Arm 42 is mounted on the upright plate 40B in a manner so as to rotate about an axis XX which extends normal to the upright plate 40B and parallel to bottom plate 40A. Arm 42 includes an arcuate portion 46 which supports a slidable carriage 48. Tool translation table 22 is attached to a bracket 49 fixed to the carriage 48 and carries a surgical tool 50 having a tip 51. The head positioning means 24 is supported on the bottom plate 40A for moving the head 52 of a patient, fixed therein, to a location so that the tool entry point on the eye 14 coincides with point P.

Figure 3:
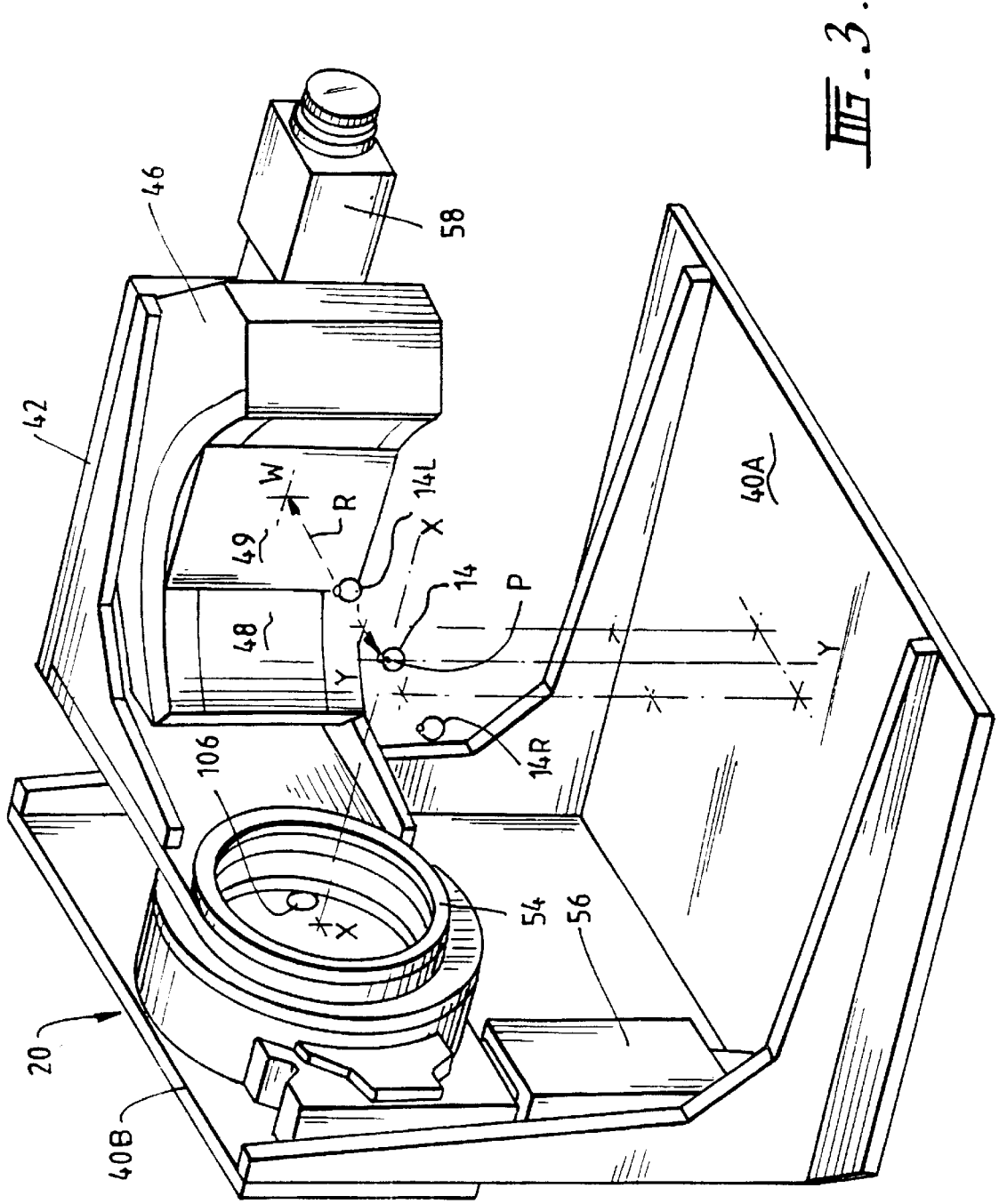
FIG. 3 is a perspective view of a stereotactic manipulator incorporated in the system shown in FIG. 1.
Figure 4:
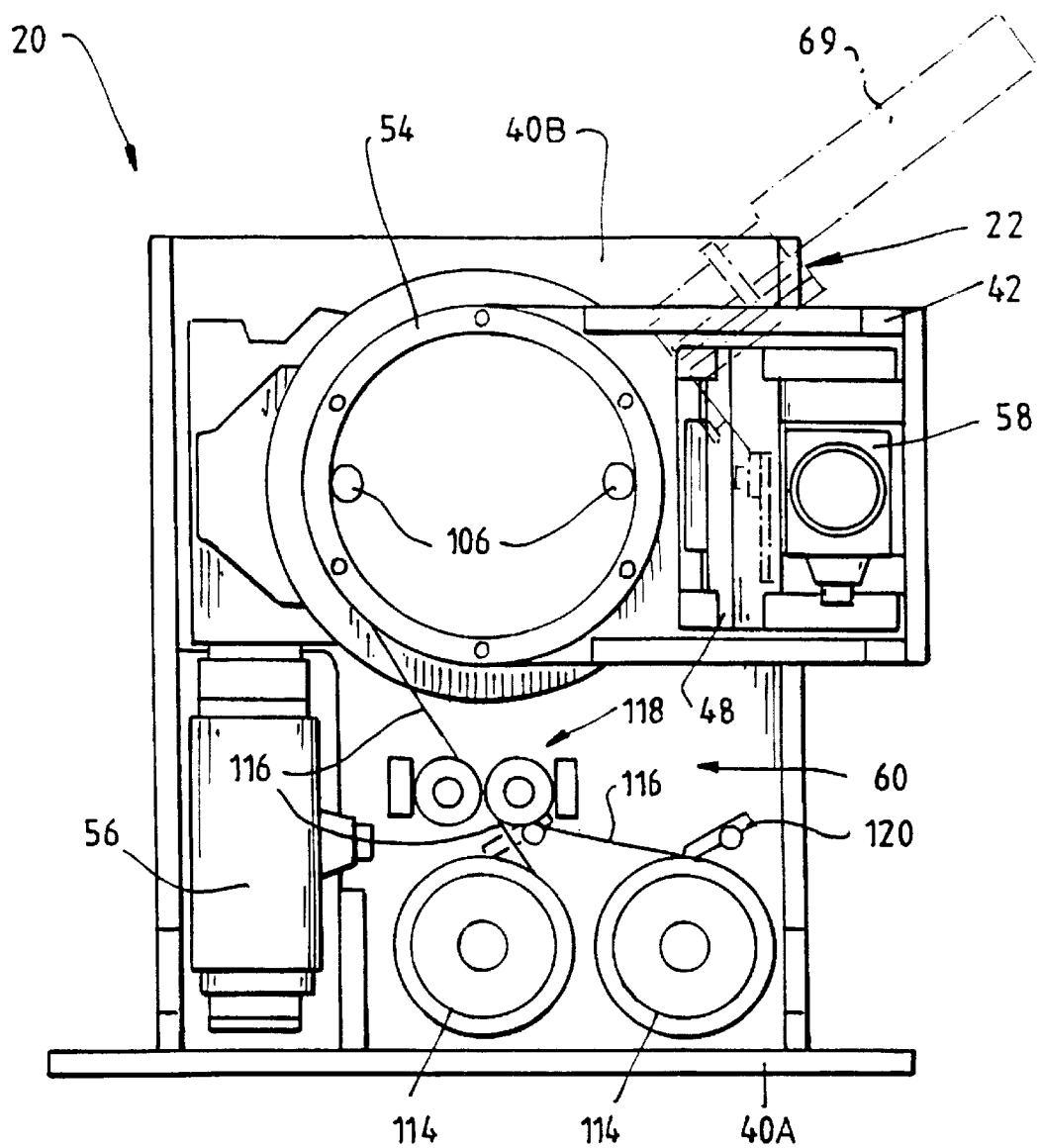
FIG. 4 is an end view of the stereotactic manipulator shown in FIG. 3 incorporating a tensioning system and showing in phantom a tool translation table.

The stereotactic manipulator 20 is shown in greater detail in FIG. 3 and 4. From these figures, it can be seen that the arm 42 is in the shape of a right angle and terminates at one end in a mounting ring 54. The mounting ring rotatably couples the arm 42 to the plate 40B in a manner so as to rotate about axis XX. The actual rotation of the arm 42 about axis XX is effected by a stepper motor 56 fastened to the upright plate 40B. The stepper motor 56 receives control signals from the surgeon 26 via joystick 34 or keyboard 36. The carriage 48 is able to slide from side to side along the curve of arcuate portion 46.

More particularly the carriage 48 in effect rotates about vertical axis YY with a constant and fixed radius R as it slides along curved portion 46 when the arm 42 is in a horizontal plane. The point P is at the intersection of axes XX and YY. The curved portion 46 and carriage 48 both have a radius of curvature equal to R. It will therefore be appreciated that for any point W fixed on, or supported by, the carriage 48 and the distance from that point W to point P will remain constant irrespective of the rotation of arm 42 about axis XX or motion of carriage 48 along curved portion 46. This is critical to the marker 16 as explained hereinafter.

When ultramicrosurgery is to commence the eye 14 is located so that the tool incision and entry point coincides with point P. In FIG. 3, eyes 14R and 14L represent the typical spacing of a patient's eyes relative to the actual operating position shown by eye 14. The head position means 24 (refer FIGS. 1 and 2) is operated to move the eye(s) 14R, 14L to the position shown for eye 14.

The sliding motion of the carriage 48 is effected by stepper motor 58 which is also under control of the surgeon 26 via joystick 34 and/or keyboard 36. A goniometer such as model no. BG 160 manufactured by NEWPORT CORPORATION can be used as the stereotactic manipulator 20.

FIG. 4 illustrates an end view of the stereotactic manipulator 20 shown in FIG. 3 but with the tool translation table 22 in its mounted position shown in phantom and also depicting a counterbalance system 60. The table 22 is attached to the carriage 48 so that the length of the table 22 runs at an angle of approximately 40° to the horizontal.

Figure 5:
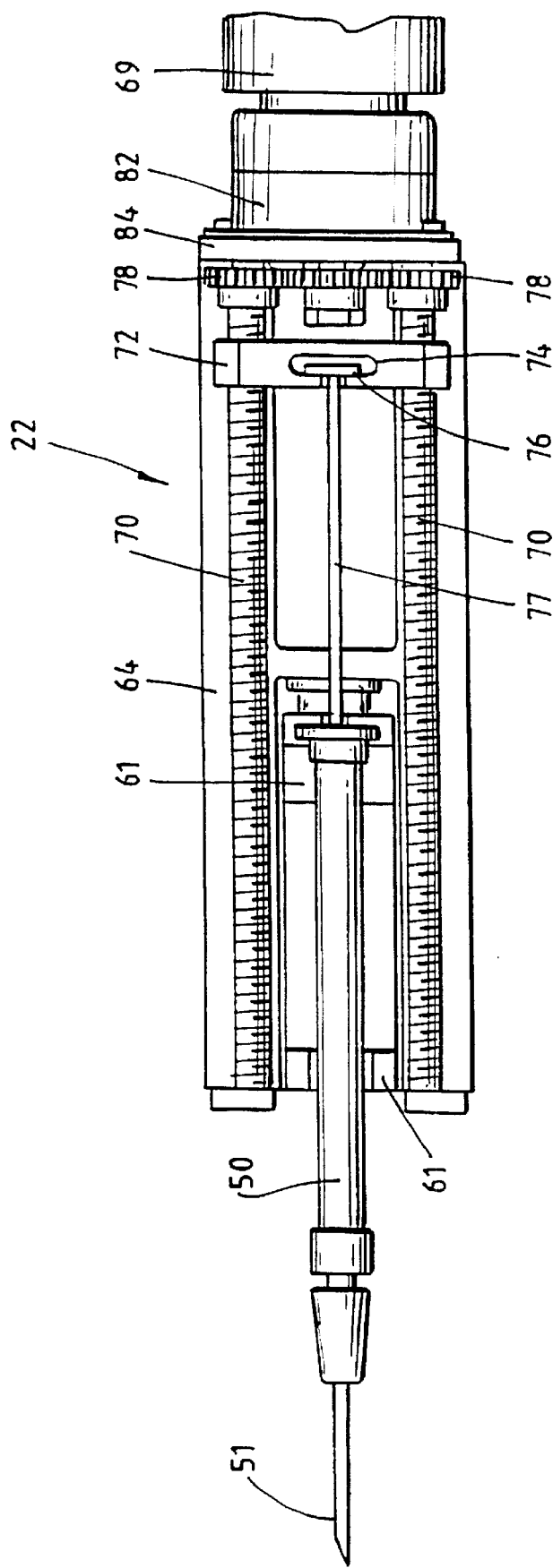
FIG. 5 is a top view of a conceptual drawing of one possible form of the tool translation table shown in FIG. 4 with a surgical tool attached.
Figure 6:
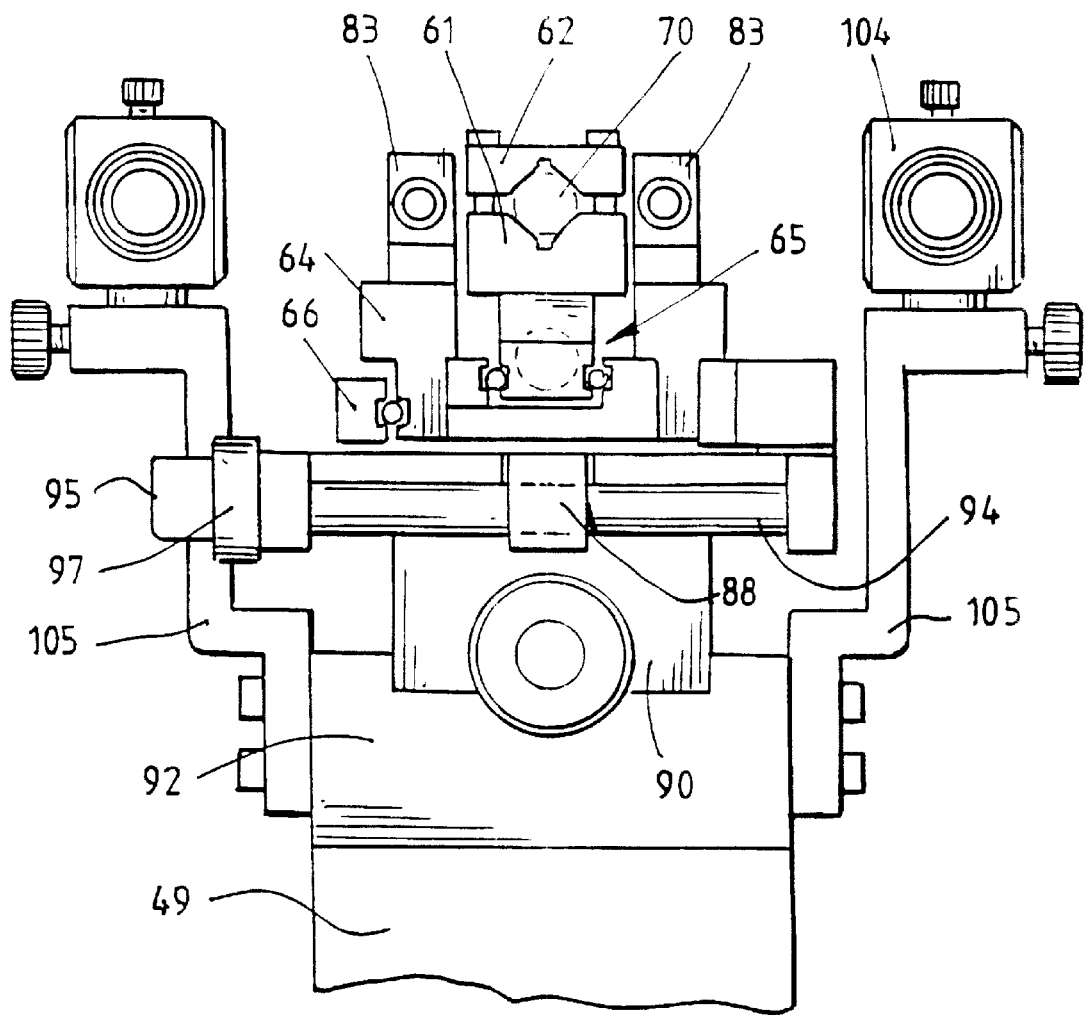
FIG. 6 is a front end view of the tool translation table (without the surgical tool attached)
Figure 7:
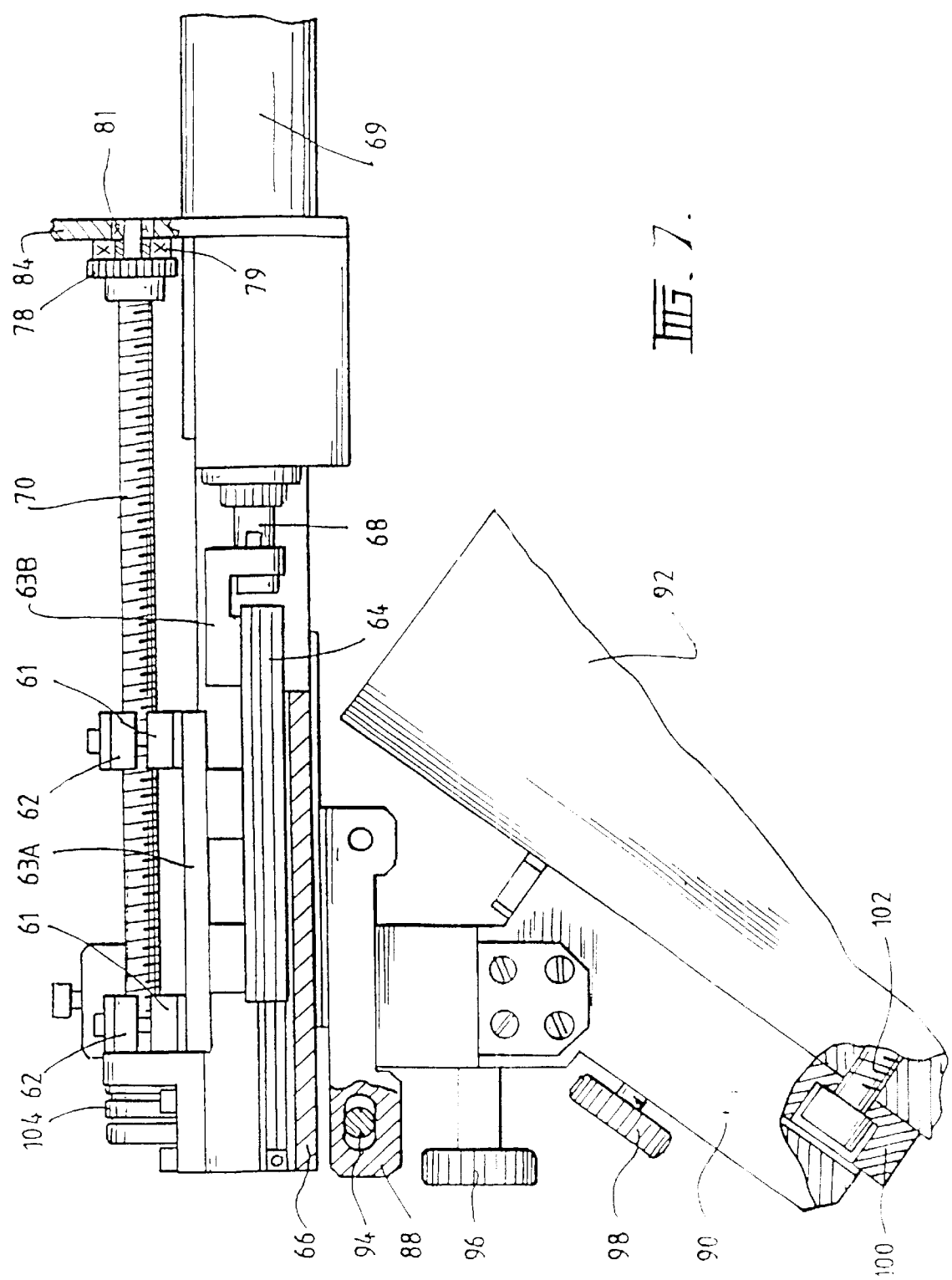
FIG. 7 is a side view in partial section of the tool translation table shown in FIG. 6; and, FIG. 8 is a side view and partial section of a portion of a means for marking the position of a predetermined point on the eye used in the system shown in FIG. 1.

Further details of the tool translation table 22 are shown in FIGS. 5 to 7. The surgical tool 50 is seated on racks 61 and clamped in place by pressing blocks 62 (see FIGS. 6 and 7). Connecting bracket 63A attach the racks 61 and thus tool 50 to a slide 64. Also attached to slide 64 by a further bracket 63B is a telescopic shaft 68 of a piezoelectric drive 69. The slide 64 sits in a bearing block 66. Energising the piezoelectric drive 69 drives shaft 68 causing linear motion of slide 64 therefore advancing or retracting tool 50. Further linear motion is allowed for between racks 61 and slide 64 by way of a slide coupling 65 using a manual wheel (not shown). This is to enable fine adjustment of the position of the tip 51 of tool 50 prior to commencement of surgery arising from defects in the manufacture of the tool (ie. for tips 51 which are not perfectly straight, or off centre relative to body of tool 50).

As seen most clearly in FIG. 5, a pair of lead screws 70 extend longitudinally on opposite sides of the tool 50 and are coupled with the body 66. Slide 72 extends transversely between and is threadingly coupled with each of the lead screws 70. The slide 72 is provided with a recess 74 which receives head 76 of an operating plunger 77 of the tool 50. A gear 78 is fixed to an upper end of each lead screw 70. Disposed between and meshing with the gears 78 is a gear set 80 which is driven by stepper motor 82 (shown only in FIGS. 5 and 7). The stepper motor 82 is attached to a wall board 84 which extends upright from and is attached to the body 66. One end of each screw 70 is held in thrust race 79 (see FIG. 7) and a bearing 81 which sits in the wall board 84. The opposite end of each screw is rotatably held in bearing block 83 (see FIG. 6).

Operation of the stepper motor 82 causes rotation of the gear set 80 which in turn impart torque to gears 78 and thus rotates the corresponding lead screws 70. As the lead screws 70 rotate, the slide 72 moves linearly along the lead screws in a direction depended upon the direction of rotation of the lead screws 70. In this way, the plunger 77 can be pushed down or pulled up to operate the tool 50.

Base 86 (see FIGS. 6 and 7) of the tool translation table 22 is pivotally coupled to underlying bracket 88. The bracket 88 is in turn fixed to slidable bracket 90. The bracket 90 is fixed to fastening block 92 which in turn is attached via bracket 49 to the carriage 48 of the stereotactic manipulator 20. Bracket 88 allows pivoting of the tool translation table 22 about a pin 94 which extends in a horizontal plane transversely to the direction of the length of table 22. The degree of pivoting about pin 94 can be effected either by a manually operated thumb wheel 95 or by a stepper motor (not shown) or other actuator (such as a pneumatic or hydraulic actuator) under the control of the surgeon 26 via computer 32. In the case of the provision of thumb wheel 95, a lock nut 97 is provided to lock the position of the table 22 about pin 94.

The bracket 90 is also configured to provide positional adjustment of table 22 in a sideways direction perpendicular to its length by turning of thumb screw 96. However, in an alternate embodiment, it is envisaged that the motion of the bracket 90 can also be controlled by a stepper motor or other actuator via computer 32. The positional adjustments to the table 22 which can be made by the bracket 88 and/or bracket 90 as well as between slide 64 and bearing block 65 are provided to correct for possible defects in the manufacture of the tool 50 and in particular, the operation tip 51 of the tool. In particular, these adjustments are made to compensate for tips 51 which may not be precisely straight or off centre. Screw 98 (see FIG. 7) fixes the bracket 90 to an underlying mounting rail 100 which in turn is fastened to the block 90 via bolt 102.

The marker 16 for visually designating point P comprises a first pair of lasers 104 which are mounted on the tool translation table 22 on opposite sides of the tool 50 (refer FIGS. 5 and 6) and a second pair of lasers 106 (refer FIGS. 3, 4 and 8) which are fixed to the upright plate 40B of the stereotactic manipulator 20. The lasers 104 and 106 are set so that their respective laser beams intersect at point P.

Lasers 106 are fixed to the plate 40B and therefore, after initial setting, do not move with rotation of the arm 42. However, lasers 104 are attached by brackets 105 to block 92 and therefore move with arm 42 and carriage 48. This movement does not cause the beams from the lasers 104 to deviate from point P. This is due to the previously described relationship between axes XX, YY, radius R and point W (refer FIG. 3). Because the lasers 104 are fixed to move with carriage 48 and arm 42, once they are aligned to pass through point P they will always pass through that point irrespective of the rotation of arm 42 about axis XX or motion of carriage 48 about axis YY.

As previously mentioned, the point P defines the point on the eye 14 through which tip 51 of tool 50 passes into the eye 14. The intersection point of the beams from lasers 104 and 106 is a point in free space whereas the point P is a physical location on the eye 14. In order for the intersection point of the laser beams to coincide with point P, it is generally necessary to move the head 52 of the patient to a position so point P coincides with the intersection point of the laser beams.

As previously discussed in relation to FIG. 2, this is achieved by fixing the head 52 of a patient into head positioning means 24 and then by this means, moving the head 52 so that the point P coincides with the intersection point of the laser beams and thus can be visualised on eye 14. To this end, the head positioning means 24 comprises a brace 110 which is fixed to an XYZ positioner 112. Movement of the XYZ positioner in each of the X, Y and Z directions is effected by separate stepper or DC motors (not shown) which can be controlled by the surgeon 26 via a joystick 35 (refer FIG. 1) and/or the keyboard 36.

To reduce the load on stepper motor 56, counterbalance system 60 (refer FIG. 4) is operatively coupled to the arm 42. It will be appreciated that the load on motor 52 will vary considerably depending on the rotational position of the arm 42 about axis XX. When the arm 42 is in a substantially horizontal plane, the load on the motor 52 will be at a maximum whereas when the arm 42 is in a vertical plane, the load on motor 56 will be at a minimum. The counterbalance system 60 comprises a pair of spring loaded pulleys 114 about which extend steel wires 116. The steel wires 116 pass through a pair of rollers 118 and are then attached to the mounting ring 54. The springs of the pulleys 114 can be preloaded to a predetermined tension by use of an integral ratchet (not shown) and pawl 120. The greater the degree of rotation of the arm 42 from a vertical position to a horizontal position, the greater the tension on the wire 116 and therefore the greater the counterbalancing effect.

The stereotactic manipulator 20, tool translation table 22, stepper motors, and other components of the system 10 are preferably selected to have tolerances which enable the overall positioning inaccuracy of the system to be preferably less than 5 microns. This can be achieved with currently commercially available equipment. For example, as previously mentioned, the stereotactic manipulator 20 can be in the form of a BG 160 goniometer from NEWPORT CORPORATION and the drive 69 for providing linear motion of the tool 50 can be a linear positioner with piezoelectric drive such as the BURLEIGH linear translator.

The tool 50 carried by the tool translation table 22, can be changed during microsurgery to perform specialised functions. For example, initially, the surgical tool 50 could be in the form of a diamond drill for making a hole at point P through the sclera of the eye 14. If it is desired to inject a layer of the retina with a particular drug, the tool 50 can be replaced with a micropipette to provide pico injection of a desired drug to one of the layers of the retina. Alternately, if it is desired to remove scar tissue, the tool 50 can be a pair of microscissors.

The method of operation of the system 10 will now be described in detail.

Initially, the eye 14 of a patient is immobilised by clamping with eye ring 12 and the head 52 of the patient then fixed into head brace 110. Lasers 104 and 106 are energised to define a point in space which ultimately will form the incision point and pivot point P of tool 50. XYZ positioner 112 is operated by the surgeon 26 via joystick 35 or keyboard 36 so as to move the eye 14 to a location at which the intersection points of the lasers 104 and 106 coincide with and thereby mark point P on the eye 14. The surgeon 26 is able to visualise the coincidence of point P with the intersecting beams of lasers 104 and 106 through the microscope 28. An incision or hole is made at point P by fastening an appropriate surgical tool 50 to the table 22 and moving the tool 50 via the stereotactic manipulator 20 and tool translation table 22 with joystick 34 so that the tip 51 of the tool is brought into contact with point P on the eye 14. By further manipulation of the joystick 34, the surgeon 26 can energise the piezoelectric motor 69 to move the tip of the tool 106 linearly to pierce the eye 14 at point P.

If it is desired to deliver a pico injection of a particular drug to a layer of the retina, the tool 50 on table 22 is first withdrawn from the eye 14 and then replaced with a micropipette. The tip of the micropipette is align with point P and then moved linearly into the eye 14 again by operation of the piezoelectric drive 69. The specific location in which the pico injection drug is to be delivered can be arrived at by pivoting the micropipette about point P by a combination of rotation of the arm 42 about axis XX or the sliding of the carriage 48. Because point P forms a pivot point for the tool 50, such motion does not induce any pressure on the sclera of the eye. When the tip of the micropipette is at the desired location, the surgeon 26 can then via joystick 34 or keyboard 36 operate the stepper motor 82 to turn the lead screws 70 thereby forcing the slide 72 to move linearly in a downward direction pushing plunger 77 of the micropipette to deliver the desired dosage of drug.

The micropipette can then be withdrawn again with the control of the surgeon 26 via joystick 34/keyboard 36 and the incision point P sutured.

It will be appreciated that all motion of the surgical tool 50 is achieved by the surgeon 26 manipulating the remote controller 30. At no time does the surgeon's hand actually cause motion of the surgical tool 50 while in use. Adjustment of tool translation table 22 by brackets 88 and 90, if necessary to compensated for defects in tools 50, is performed prior to insertion of the tool 50 into the eye 14. In this way, the surgeon's hand is physically isolated from the surgical tool 50. Further, owing to the positional accuracy of the components of the system, the surgeon is able to perform precise ultramicrosurgery without fear of causing extraneous damage due to normal hand tremor.

Experiments conducted to date on rat eyes which are significantly smaller than human eyes indicate that the system 10 can successfully operate with positional accuracy and repeatability in the order of 1 micron with current commercially available components.

By adding a digitising tablet (not shown) to the remote controller 30 and moreover the computer 32, surgery performed by the system 10 can be semi or fully automated. In particular, the surgeon 26 can view on a digitising tablet a projection of the retinal image derived from microscope 28. From this, the surgeon can stereo-visually identify the operation site on the retina. The three dimensional co-ordinates of the operation sight can then be passed to the computer 32 with identification of the appropriate pars plana for the insertion point P of tool 50. The three dimensional location of the point P may be entered by the surgeon 26 selecting with the digitising tablet two or the three dimensions and the third dimension may be communicated to the computer 32 via an encoder (not shown) which reports the position of focusing elements of the microscope 28. Alternately, a laser surface scanning device (not shown) can be used to perform this measurement, as used by Hunter et al to model the exterior surface of the eye and cornea [ Hunter et al 1993]. That is, the surgeon 26 can specify a particular location for the tip 51 of the tool 50 say via keyboard 36 and the digitising tablet (if provided) so that the stereotactic manipulator 20 and tool translation table 22 are operated under programmed control of the computer 32 and measurement and control unit 38 to dispose the tip 51 of the tool 50 at a desired location within the eye 14.

In a further variation to the system 10 it is envisaged that sensory feedback may be provided to the joystick 34 to enable the surgeon 26 to sense the force exerted on the tip 51 of the surgical tool 50 due to reaction of tissue in contact with the surgical tool 50.

Further, the eye ring 12 can also be driven with motors or actuators (not shown) to change the position of the eye 14.

In the system 10 as presently described and illustrated, the tool 50 on the tool translation table 26 is manually changed to perform specific functions. However, it is anticipated that tools 50 can be changed automatically for example by means of a turret arrangement in which a number of different tools are loaded which can subsequently be fixed to the tool translation table 22.

In use, embodiments of the system 10 according to the current invention has substantial advantages over the current manual techniques of performing eye surgery on humans. The high positioning accuracy of the system 10 enables injection of drugs into retinal veins or tissues, presenting the possibility that compounds may be injected into the subretinal tissue or blood vessels without causing damage or bleeding. The system also enables the provision of an outpatient service for eye surgery, involving the use of local anaesthetics, which is made possible because of the reduction in operation time which the semi-automated design of the system allows. An entire class of eye operations which have been developed only in a research environment are now made feasible for routine surgery, and it is expected that the success rate of such operations will improve markedly.

The system 10 may be used in many current ocular surgical procedures and opens the way to a new era of controlled and localised treatment in a surgical settings for such diseases as age-related macular degeneration (incidence in USA 30 million persons over 40 years of age), retinal vein occlusion (incidence in USA 2.1 four per 1000 persons), diabetic retinopathy (incidence in USA 2–4 per 100 persons, glaucoma and retinitis pigmentosa).

Future surgical techniques for which the current invention may be applicable include retinal transplantation such as tissue engineered perivascular endothelial cell implants [ Nathan et al 1995], the installation of pre-retinal membranes to treat retinal detachment, gene therapy for blood vessel treatment [ Willard et al 1994], installation of an artificial retainer [ Roush 1995], and excimer laser delivery.

Modifications may be made to the invention as will be apparent to a person skilled in the art of surgical system design. For example, any surgical tool including microcutters, microforceps, microdissectors or microimplanters can be loaded onto and worked by the systems 10. Also, by use of a high resolution 3 dimensional camera in line with the microscope 28 the surgeon is able to use the system 10 for teleoperations. That is performing surgery at a location remote from the patient, for example several kilometres away from an operating theatre, or even from a different country. There is no necessity for the surgeon to be in the same room as the patient. These and other modifications may be made without departing from the ambit of the invention, the nature of which is to be ascertained from the foregoing description and the appended claims.

REFERENCES

The following is a list of the references contained in the above description:

Allf and de Juan Jr 1987
  B. E. Allf and ES. de Juan Jr. In Vivo Cannulation of Retinal Vessels, *Greafe's Arch Clin Exp Opthalmol* (1987) 225:221–225
Benner et al 1993
  Jeffrey D Benner et al A Glass Micropipette Holder for Opthalmic Surgical Procedures *Americal Journal of Ophthalmology* Vol 116 No. 4 511–512 (1993)
Hunter et al 1993
  Ian W. Hunter et al A Teleoperated Microsurgical Robot and Associated Virtual Environment for Eye Surgery *Presence Vol* 2 No 4 Fall 1993, 265–280
Nathan et al 1995
  Nathan et al, *Proc Natl Acad Sci USA* 92:8130–8134 (1995)
Roush 1995
  W. Roush, *Science* 268:637–638 (1995)
Toth et al 1992
  Cynthia A. Toth et al, Ultramicrosurgical Removal of Subretinal Hemorrhage in Cats *Americal Journal of Opthalmology* 113:175–182 (1992)
Willard et al 1994
  J. E. Willard et al *Circulation* 89:2190–2197 (1994)

The claims defining the invention are as follows:

1. A system for ocular ultramicrosurgery comprising:
   means for immobilising an eye of a patient on which ultramicrosurgery is to be performed;
   means for marking a position of a predetermined point on said eye;
   tool support and positioning means for supporting an elongate tool so that said tool is moved with positional accuracy (a) to cause a tip of said tool to enter said eye at said predetermined point and (b) thereafter to cause said tool to pivot about said predetermined point whereby said tip is positioned to any desired location within the eye to perform ultramicrosurgery; and
   remote control means for remotely controlling the position and operation of said tool, said remote control means physically isolating the hands of a surgeon from said tool;
      whereby, in use, a surgeon can, by said remote control means, position said tool to perform ultramicrosurgery.

2. A system according to claim 1, wherein said means for marking the position of a predetermined point comprises means for defining a point in space.

3. A system according to claim 2,.wherein said means for defining a point in space comprises at least two lasers supported in different planes and arranged so that their respective laser beams intersect in space, said point in space being the point of intersection of said laser beams.

4. A system according to claim 3, further comprising means for moving said eye and said point in space relative to each other so that said point in space can be bought to coincide with said predetermined point.

5. A system according to claim 4, wherein said means for moving said eye and said point in space relative to each other comprises head fixing means for fixing the position of a head of the patient and, means for moving said head fixing means in three orthogonal planes under control of said remote control means.

6. A system according to claim 5, wherein said tool support and positioning means comprises: a stereotactic manipulator providing two degrees of freedom of movement of said tool to allow pivoting of said tool about said predetermined point; and, a tool translation table supported on said stereotactic manipulator providing at least one further degree of freedom of movement of said tool and enabling said tool to be moved linearly into and out of said eye through said predetermined point.

7. A system according to claim 6, wherein said tool translation table is supported with at least one degree of freedom on said stereotactic manipulator so that the position of the tip of said tool can be adjusted to compensate for defects in the structure or form of the tip.

8. A system according to claim 7, wherein said tool translation table is further provided with at least one actuator under control of said remote control means to operate or work said tool.

9. A system according to claim 6, wherein one pair of lasers is supported on said tool translation table, said one pair of lasers being arranged so that their respective laser beams mutually intersect each other at said predetermined point; and, wherein a second pair of lasers is supported on said stereotactic manipulator in a plane different to that containing said one pair, said second pair of lasers being arranged so that their respective laser beams mutually intersect each other at said predetermined point.

10. A system according to claim 1, wherein said remote control means comprises a computer operatively associated with said tool support and position means, said being computer provided with a device for receiving instructions from a surgeon to manipulate and control the position and operation of said tool.

* * * * *